(12) United States Patent
Eisermann et al.

(10) Patent No.: US 7,569,074 B2
(45) Date of Patent: Aug. 4, 2009

(54) EXPANDABLE INTERVERTEBRAL IMPLANT

(75) Inventors: Lukas Eisermann, Memphis, TN (US); Paul Geibel, San Antonio, TX (US); Jeffrey Zhang, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 701 days.

(21) Appl. No.: 10/734,041

(22) Filed: Dec. 11, 2003

(65) Prior Publication Data

US 2005/0131536 A1    Jun. 16, 2005

(51) Int. Cl.
*A61F 2/44* (2006.01)
(52) U.S. Cl. .................................... 623/17.11
(58) Field of Classification Search ... 623/17.11–17.16; 606/61
See application file for complete search history.

(56) References Cited

U.S. PATENT DOCUMENTS

| | | | |
|---|---|---|---|
| 4,863,476 A | 9/1989 | Shepperd | |
| 5,059,193 A * | 10/1991 | Kuslich | 606/61 |
| 5,522,899 A | 6/1996 | Michelson | |
| 5,554,191 A | 9/1996 | Lahille et al. | |
| 5,609,635 A | 3/1997 | Michelson | |
| 5,653,763 A | 8/1997 | Errico et al. | |
| 5,658,335 A | 8/1997 | Allen | |
| 5,665,122 A | 9/1997 | Kambin | |
| 5,776,199 A | 7/1998 | Michelson | |
| 5,782,832 A | 7/1998 | Larsen et al. | |
| 6,080,193 A | 6/2000 | Hochshuler et al. | |
| 6,102,950 A | 8/2000 | Vaccaro | |
| 6,117,174 A | 9/2000 | Nolan | |
| 6,129,763 A | 10/2000 | Chauvin et al. | |
| 6,176,882 B1 | 1/2001 | Biedermann et al. | |
| 6,190,414 B1 | 2/2001 | Young et al. | |
| 6,371,989 B1 | 4/2002 | Chauvin et al. | |
| 6,436,140 B1 | 8/2002 | Liu et al. | |
| 6,610,089 B1 | 8/2003 | Liu et al. | |
| 2002/0040243 A1 | 4/2002 | Attali et al. | |
| 2002/0107574 A1 | 8/2002 | Boehm et al. | |
| 2003/0130739 A1 | 7/2003 | Gerbec et al. | |

FOREIGN PATENT DOCUMENTS

| | | |
|---|---|---|
| DE | 44 16 605 C1 | 6/1995 |
| DE | 203 14 708 U1 | 11/2003 |
| WO | WO 97/00054 | 1/1997 |
| WO | WO 00/12033 | 3/2000 |
| WO | WO 01/68005 | 9/2001 |

OTHER PUBLICATIONS

Coda, http://www.spinalconcepts.com/products/code.html, Jun. 8, 2005, Copyright 2004 Spinal Concepts, 1 page.

* cited by examiner

*Primary Examiner*—Eduardo C Robert
*Assistant Examiner*—David Comstock

(57) ABSTRACT

An expandable intervertebral implant including a body having a longitudinal axis and including first and second axial walls spaced apart along a transverse axis, and first and second transverse end walls extending between and interconnecting the first and second axial walls. The intervertebral implant includes an expansion member co-acting with the axial walls to expand the body along the transverse axis.

54 Claims, 3 Drawing Sheets

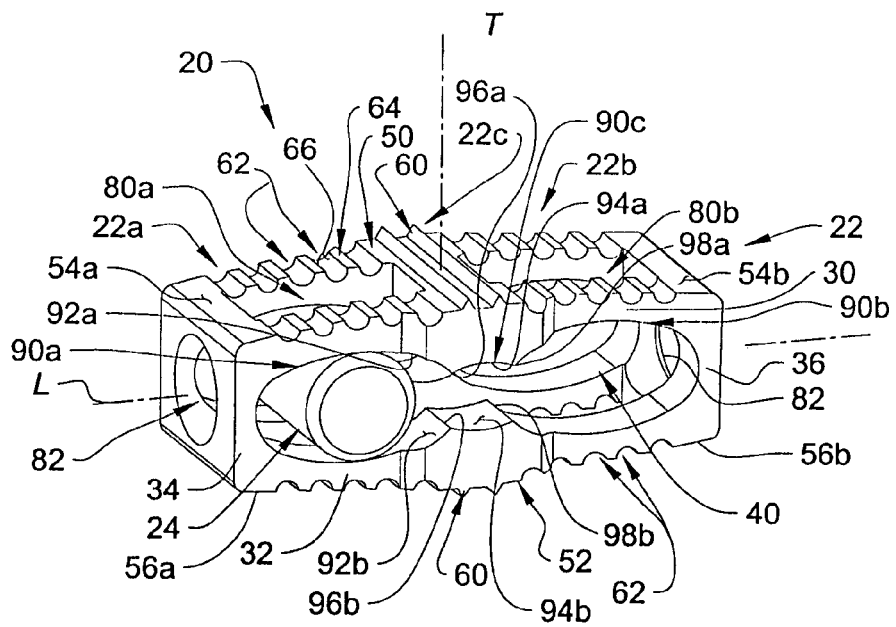
Fig. 1
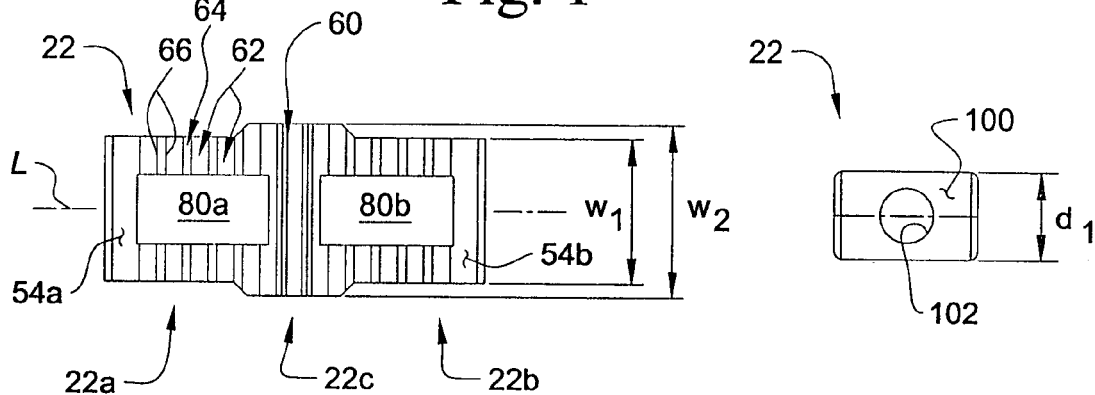
Fig. 3
Fig. 5
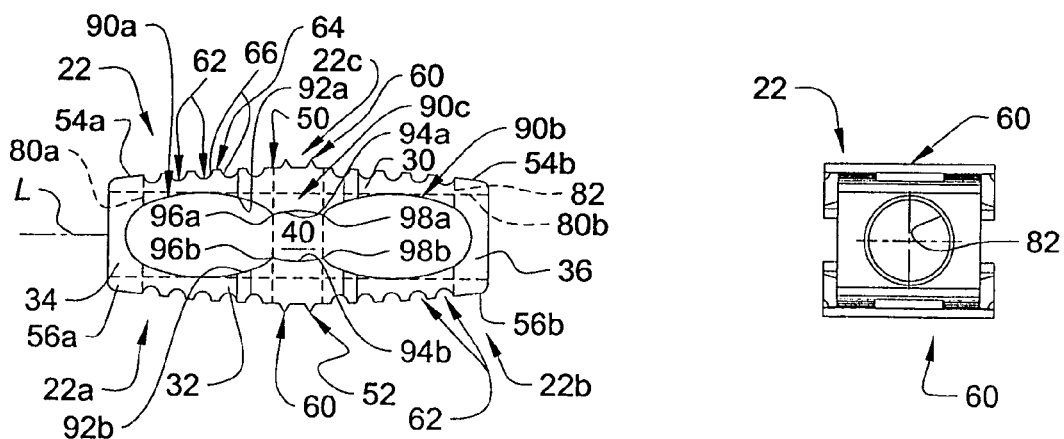
Fig. 2
Fig. 4

EXPANDABLE INTERVERTEBRAL IMPLANT

FIELD OF THE INVENTION

The present invention relates generally to the field of intervertebral implants, and more particularly relates to an expandable intervertebral implant.

BACKGROUND

There have been numerous attempts to develop intervertebral implants to replace a damaged or degenerated natural spinal disc and to maintain sufficient stability of the disc space between adjacent vertebrae, at least until arthrodesis is achieved. Intervertebral implants can either be solid, sometimes referred to as a spacer or plug, or can define a hollow interior designed to permit bone in-growth, sometimes referred to as a fusion device or fusion cage. The interior of a fusion device may be filled with a bone growth inducing substance to facilitate or promote bone growth into and through the device to achieve a more rapid and stable arthrodesis.

Various types, shapes and configurations of intervertebral implants are known in the art. For example, one of the more prevalent designs includes intervertebral implants having a cylindrical shape and defining external threads to facilitate insertion into the disc space. As a result, reaming and tapping the adjacent vertebral bodies is required to form a threaded passage for receiving the threaded implant. However, these techniques generally involve over-reaming of the posterior portion of the adjacent vertebral bodies, thereby resulting in excessive removal of load bearing vertebral bone which may lead to instability of the portion of the spinal column being treated. Other types of intervertebral implants have a generally rectangular configuration having planar upper and lower outer surfaces for engagement with adjacent vertebral bodies. However, the planar upper and lower outer surfaces may not adequately conform to the shape of the vertebral endplates, thereby resulting in non-uniform and inconsistent engagement between the implant and the adjacent vertebral bodies.

Additionally, most intervertebral implant designs have a predetermined, fixed height that approximates the natural height of the disc space. Insertion of an intervertebral implant having a fixed height usually requires distraction of the disc space to an insertion height somewhat greater than the natural height of the disc space. Attempts have also been made to develop various types of expandable intervertebral implants that are configured to expand along the height of the disc space. These types of expandable implants typically include multiple arms or branches having proximal end portions that extend from a fixed base, and distal end portions that remain unconnected and free to move independently of one another. A wedge is displaced between the arms to separate or splay the distal end portions of the arms apart to transition the implant to an expanded configuration defining a taper and having a maximum implant height adjacent the distal end portion of the implant. Notably, positioning of the wedge adjacent the distal end portions of the arms fails to provide support along the mid-portion of the implant to resist compression forces exerted onto the implant by the adjacent vertebral bodies. Additionally, the expansion wedge may occupy a significant portion of the inner chamber of the implant, thereby reducing the capacity of the implant to receive bone growth inducing material therein.

Thus, there is a general need in the industry to provide an improved expandable intervertebral implant. The present invention satisfies this need and provides other benefits and advantages in a novel and unobvious manner.

SUMMARY

The present invention relates generally to an expandable intervertebral implant. While the actual nature of the invention covered herein can only be determined with reference to the claims appended hereto, certain forms of the invention that are characteristic of the preferred embodiments disclosed herein are described briefly as follows.

In one form of the present invention, an expandable intervertebral implant is provided, including a body having a longitudinal axis and including first and second axial walls spaced apart along a transverse axis, said first axial wall including a first pair of opposite end portions and second axial wall including a second pair of opposite end portions, with the first pair of end portions interconnected with the second pair of end portions. The implant also includes an expansion member that co-acts with the first and second axial walls to expand the body along the transverse axis.

In another form of the present invention, an expandable intervertebral implant is provided, including a body having a longitudinal axis and including first and second axial walls spaced apart along a transverse axis, and first and second transverse end walls extending between and interconnecting opposing end portions of the first and second axial walls. The implant also includes means for expanding the first and second axial walls along the transverse axis.

In another form of the present invention, an expandable intervertebral implant is provided, including a body having a longitudinal axis and including first and second axial walls extending generally along the longitudinal axis and spaced apart along a transverse axis. The implant also includes an expansion member co-acting with the first and second axial walls to expand the body along the transverse axis such that the first and second axial walls are outwardly deformed to define a convex outer curvature along the longitudinal axis.

In another form of the present invention, an expandable intervertebral implant is provided, including a body having a longitudinal axis and including first and second axial walls spaced apart along a transverse axis, and first and second transverse end walls extending between and interconnecting opposing end portions of the first and second axial walls. The implant also includes an expansion member co-acting with the first and second axial walls to transition the body from an initial configuration to an expanded configuration wherein the first and second axial walls are outwardly deformed away from one another along the transverse axis.

In another form of the present invention, an expandable intervertebral implant is provided, including a fusion cage having a longitudinal axis and including first and second axial walls extending generally along the longitudinal axis and spaced apart along a transverse axis. The fusion cage defines an inner chamber having a central portion and opposite end portions. An expansion member is positioned within the central portion of the inner chamber and co-acts with the first and second axial walls to expand the body along the transverse axis. A bone growth promoting material is positioned within the first and second end portions of the inner chamber on opposite sides of the expansion member.

In another form of the present invention, a surgical method is provided, including providing an expandable intervertebral implant having a longitudinal axis and including first and second axial walls spaced apart along a transverse axis and first and second transverse end walls extending between and interconnecting opposing end portions of the first and second axial walls, inserting the intervertebral implant within an intervertebral space with the first and second axial walls positioned adjacent respective first and second vertebral bodies, and expanding the first and second axial walls along the transverse axis to engage the first and second axial walls against the respective first and second vertebral bodies.

It is one object of the present invention to provide an improved expandable intervertebral implant. Further objects, features, advantages, benefits, and aspects of the present invention will become apparent from the drawings and description contained herein.

BRIEF DESCRIPTION OF THE DRAWINGS

FIG. 1 is a perspective view of an expandable intervertebral implant according to one form of the present invention.

FIG. 2 is a side elevational view of an expandable fusion cage according to one embodiment of the invention for use in association with the intervertebral implant illustrated in FIG. 1.

FIG. 3 is a top plan view of the expandable fusion cage illustrated in FIG. 2.

FIG. 4 is an end view of the expandable fusion cage illustrated in FIG. 2.

FIG. 5 is a side elevational view of an expansion member according to one embodiment of the invention for use in association with the intervertebral implant illustrated in FIG. 1.

DESCRIPTION OF THE PREFERRED EMBODIMENTS

Figure 6:
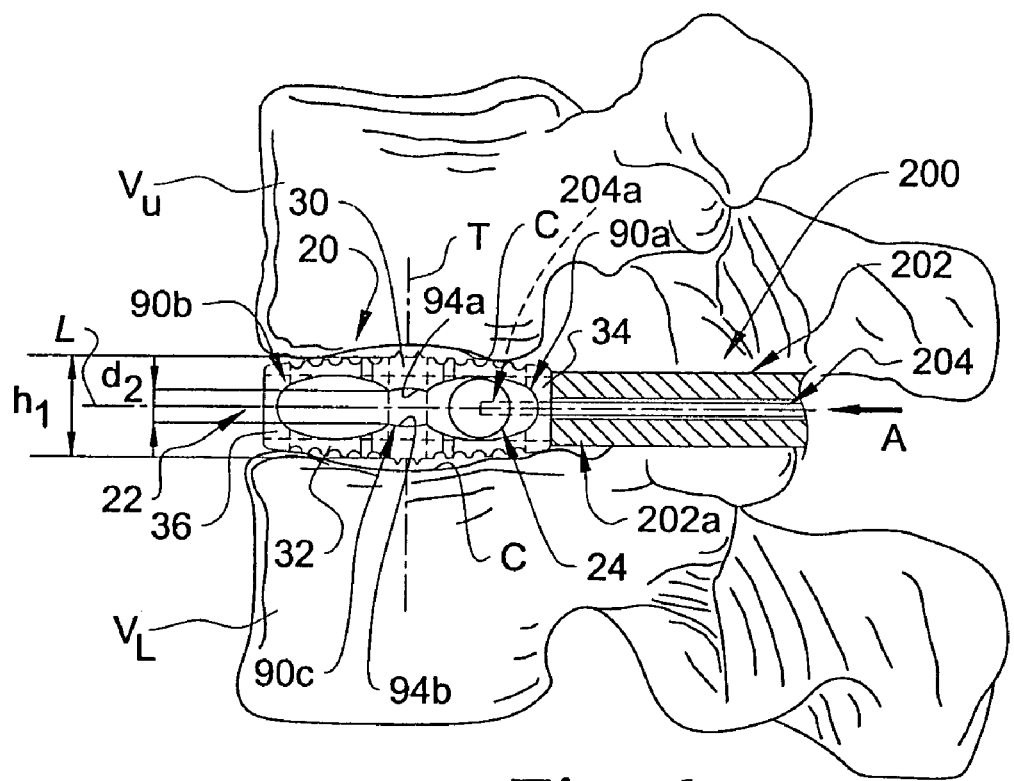
FIG. 6 is a cross-sectional side view of the intervertebral implant illustrated in FIG. 1, as positioned between adjacent vertebral bodies in a non-expanded configuration.

For the purposes of promoting an understanding of the principles of the invention, reference will now be made to the embodiments illustrated in the drawings and specific language will be used to describe the same. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

Figure 7:
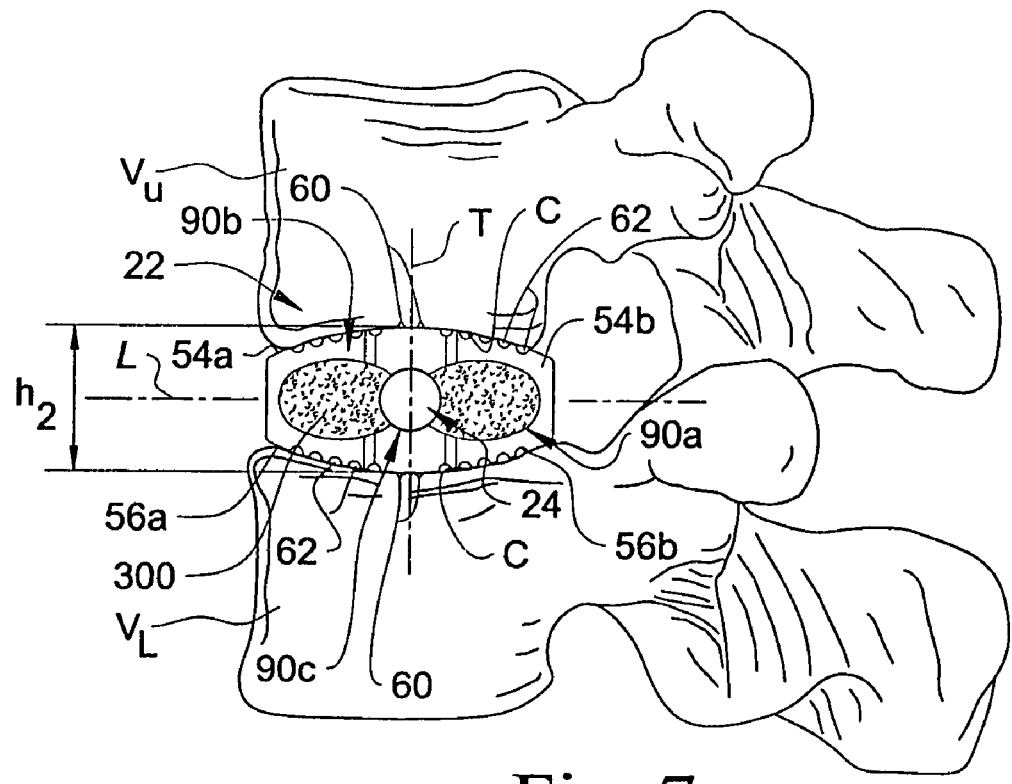
FIG. 7 is a cross-sectional side view of the intervertebral implant illustrated in FIG. 1, as positioned between adjacent vertebral bodies in a fully expanded configuration.

Referring to FIG. 1, shown therein is an intervertebral implant 20 according to one form of the present invention. The intervertebral implant 20 extends along a longitudinal axis L and is generally comprised of an expandable body 22 and an expansion member 24. As will be discussed in greater detail below, the expansion member 24 serves to transition the expandable body 22 from an initial configuration, as shown in FIG. 6, to an expanded configuration, as shown in FIG. 7, wherein expansion of the body 22 occurs generally along a transverse axis T.

The components of the intervertebral implant 20 are formed of a bio-compatible material. In one embodiment of the invention, the components of the intervertebral implant 20 are formed of a metallic material such as, for example, stainless steel and stainless steel alloys, titanium and titanium alloys, shape-memory alloys, cobalt chrome alloys, or any other suitable metallic material. In another embodiment of the invention, the components of the intervertebral implant 20 are formed of a non-metallic material such as, for example, a polymeric material, a ceramic material, a reinforced composite material, bone, a bone substitute material, or any other suitable non-metallic material.

Referring collectively to FIGS. 1-4, shown therein are further details regarding the expandable body 22. In the illustrated embodiment of the invention, the expandable body 22 is configured as an expandable fusion cage including features that facilitate or promote bone growth into and through the implant 20 to achieve arthrodesis between the adjacent vertebral bodies, the details of which will be discussed below. However, it should be understood that in other embodiments of the invention, the expandable body 22 may be configured as an expandable spacer or plug.

In one embodiment of the invention, the fusion cage 22 is comprised of upper and lower walls 30, 32 extending generally along the longitudinal axis L, and a pair of end walls 34, 36 extending transversely between and interconnecting opposing end portions of the upper and lower walls 30, 32. The upper and lower axial walls 30, 32 and the transverse end walls 34, 36 cooperate to define an inner chamber 40 extending generally along the longitudinal axis L. In the illustrated embodiment of the fusion cage 22, the axial walls 30, 32 and the transverse walls 34, 36 provide the fusion cage 22 with a generally rectangular axial cross-section. However, it should be understood that other shapes and configurations of the fusion cage 22 are also contemplated as falling within the scope of the present invention.

As illustrated in FIG. 3, the fusion cage 22 includes end portions 22a, 22b having a width $w_1$ and a central portion 22c having a width $w_2$. The width $w_2$ of the central portion 22c is somewhat greater than the width $w_1$ of the end portions 22a, 22b to provide increased surface area adjacent the mid-portion of the fusion cage 22 for engagement with the adjacent vertebral bodies. Additionally, the reduced width $w_1$ of the end portions 22a, 22b also tends to increase flexibility of the upper and lower walls 30, 32 to facilitate outward deformation of the upper and lower walls 30, 32 during expansion of the fusion cage 22. However, it should be understood that in other embodiments of the invention, the fusion cage 22 may be configured to have a substantially uniform width.

In one aspect of the invention, the upper and lower walls 30, 32 are coupled to the end walls 34, 36 in a manner that allows the upper and lower walls 30, 32 to be outwardly displaced relative to one another via the expansion member 24. In another aspect of the invention, the expansion member 24 co-acts with the upper and lower walls 30, 32 to flexibly deform the upper and lower walls 30, 32 in an outward direction relative to one another to provide for outward expansion of the fusion cage 22 generally along the transverse axis T (FIG. 7). Such outward deformation is primarily attributable to the flexible nature of the upper and lower walls 30, 32 and/or the flexible interconnection between the upper and lower walls 30, 32 and the end walls 34, 36. In one embodiment, outward deformation of the upper and lower walls 30, 32 defines a convex outer curvature extending along the longitudinal axis L (FIG. 7) which, as will be discussed below, corresponds to a concave surface curvature of the adjacent vertebral bodies. In a further aspect of the invention, the upper and lower walls 30, 32 are formed integral with the end walls 34, 36 to define a unitary, single-piece fusion cage 22. However, it is also contemplated that the upper and lower walls 30, 32 and the end walls 34, 36 may be formed separately and connected together to form a multi-piece fusion cage assembly.

The upper and lower walls 30, 32 of the fusion cage 22 define upper and lower surfaces 50, 52. In one embodiment of the invention, the upper and lower surfaces 50, 52 in turn define upper bearing surfaces 54a, 54b and lower bearing surfaces 56a, 56b adjacent the end walls 34, 36. As will be discussed below, the upper and lower bearing surfaces 54a, 54b and 56a, 56b contact and bear against the cortical rim/apophyseal ring region of the respective upper and lower vertebral bodies $V_U$, $V_L$ (FIGS. 6-8) to provide support and resistance to a substantial amount of the compressive forces exerted onto the fusion cage 22. In the illustrated embodiment of the invention, the upper and lower bearing surfaces 54a, 54b and 56a, 56b are substantially smooth and devoid of any steps, protrusions, projections or irregularities. However, it should be understood that in other embodiments, the upper and lower bearing surfaces may define anchoring features to aid in engaging and gripping vertebral bone.

In a further embodiment of the invention, the upper and lower surfaces 50, 52 of the fusion cage 22 include a number of anchor elements positioned axially between the upper and lower bearing surfaces 54a, 54b and 56a, 56b. The anchor elements are adapted for engagement with the adjacent vertebral bodies $V_U$, $V_L$ to prevent or inhibit movement of the fusion cage 22 and/or to facilitate bone growth onto the fusion cage 22 subsequent to implantation within the intervertebral disc space. In one embodiment, the anchor elements comprise a number of teeth or protrusions 60 projecting from the upper and lower surfaces 50, 52. In another embodiment, the anchor elements comprise a number of grooves 62 cut into the upper and lower surfaces 50, 52. However, it should be understood that other combinations and/or configurations of anchor elements are also contemplated for use in association with the fusion cage 22, including other features or elements extending from the upper and lower surfaces 50, 52 such as, for example, spikes, threads, ridges, bumps, surface roughening, or any other element or feature suitable for anchoring to vertebral tissue. It should also be understood that in other embodiments of the invention, the upper and lower surfaces 50, 52 of the fusion cage 22 need not necessarily include any anchor elements, but may alternatively define a substantially smooth configuration devoid of any surface projections or surface irregularities.

In the illustrated embodiment of the fusion cage 22, the teeth 60 are arranged in rows extending laterally across a central portion 22c of the fusion cage 22. Although the fusion cage 22 is shown as having two rows of teeth 60 extending from the upper and lower surfaces 50, 52, it should be understood that the inclusion of a single row of teeth or three or more rows of teeth are also contemplated. Additionally, it should be understood that the teeth 60 may be orientated in other directions such as, for example, in a direction parallel with the longitudinal axis L or arranged at an oblique angle relative to the longitudinal axis L. It should also be understood that one or more rows of teeth 60 may extend from other portions of the upper and lower surfaces 50, 52, including the end portions 22a, 22b of the fusion cage 22. In one embodiment, the teeth 60 have a triangular-shaped configuration; however, other shapes and configurations of teeth are also contemplated as falling within the scope of the present invention. As shown in FIG. 7, upon transitioning of the fusion cage 22 to an expanded configuration, the teeth 60 are engaged/impacted into the vertebral endplates of the adjacent vertebral bodies $V_U$, $V_L$ to prevent or inhibit movement of the fusion cage 22 and possible expulsion from the disc space.

In the illustrated embodiment of the fusion cage 22, the grooves 62 are arranged in rows extending laterally across the end portions 22a, 22b of the fusion cage 22. Although the fusion cage 22 is shown as having ten grooves 60 formed into each of the upper and lower surfaces 50, 52, it should be understood that any number of grooves 60 may be included. Additionally, it should be understood that the grooves 62 may be orientated in other directions such as, for example, in a direction parallel with the longitudinal axis L or arranged at an oblique angle relative to the longitudinal axis L. It should also be understood that the groove may be cut into other portions of the fusion cage 22, including the central portion 22c.

In one embodiment of the invention, the grooves 62 are formed by cutting swales or channels into the upper and lower surfaces 50, 52 which are spaced apart so as to define lands or plateaus 64 that are substantially co-planar with the upper and lower surfaces 50, 52. Edges or corners 66 are defined at the point where the grooves 62 and the lands 64 meet. In one embodiment, the grooves 62 are configured to have a groove width and a groove depth that is greater than the width of the lands 64. However, other configurations of the grooves 62 are also contemplated. Additionally, in the illustrated embodiment, the grooves 62 have a substantially circular configuration defining a substantially uniform radius or curvature. However, other shapes and configurations of the grooves 62 are also contemplated such as, for example, arcuate or bow-shaped grooves, V-shaped or U-shaped grooves, or any other suitable groove shape or configuration. As illustrated in FIG. 7, upon transitioning of the fusion cage 22 to an expanded configuration, the lands 64 engage the vertebral endplates of the adjacent vertebral bodies $V_U$, $V_L$ so as to position the grooves 62 in close proximity thereto to receive bone tissue therein and/or to facilitate bone growth onto the fusion cage 22. Additionally, the edges 66 formed between the grooves 62 and the lands 64 aid in preventing or otherwise inhibiting movement of the fusion cage 22 and possible expulsion from the disc space.

As shown most clearly in FIGS. 1 and 3, in one embodiment of the invention, the upper and lower walls 30, 32 of the fusion cage 22 define a number of bone in-growth openings or windows 80a, 80b extending through the upper and lower surfaces 50, 52 and communicating with the inner chamber 40. As should be appreciated, the bone in-growth openings 80a, 80b permit bone growth from the adjacent vertebral bodies and into and possibly through the fusion cage 22. Although the fusion cage 22 is illustrated as having a pair of bone in-growth openings 80a, 80b extending through each of the upper and lower walls 30, 32, it should be understood that the fusion cage 22 may be configured to have any number of bone in-growth openings, including a single bone in-growth opening extending along substantially the entire length of the fusion cage or three, or more bone in-growth openings positioned at various locations along the length of the fusion cage 22. Additionally, although the bone in-growth openings 80a, 80b are illustrated as having a rectangular, slot-like configuration having a slot length extending along the longitudinal axis L and a slot width extending across about one-half of the width of the fusion cage 22, it should be understood that other shapes, configuration and sizes of bone in-growth openings are also contemplated. It should further be understood that although the bone in-growth openings 80a, 80b are illustrated and described as communicating with the inner chamber 40, in other embodiments, the openings 80a, 80b need not necessarily extend entirely through the upper and lower walls 30, 32.

As shown most clearly in FIGS. 1 and 4, in the illustrated embodiment of the fusion cage 22, an axial opening 82 extends through each of the end walls 34, 36 in communication with the inner chamber 40. As will be discussed in further detail below, the axial opening 82 is sized to receive a shaft portion of an instrument therein for engagement with the expansion member 24 to facilitate transitioning of the fusion cage 22 to an expanded configuration. Additionally, the axial openings 82 also permit bone growth from the adjacent vertebral bodies into the inner chamber 40 of the fusion cage 22 from posterior and anterior directions.

As illustrated in FIGS. 1 and 2, in one embodiment of the invention, the inner chamber includes a number of distinct compartments or sections positioned along the length of the fusion cage 22. In the illustrated embodiment of the fusion cage 22, the inner chamber 40 includes end compartments 90a and 90b positioned adjacent the end portions 22a and 22b of the fusion cage 22, and an intermediate or center compartment 90c positioned adjacent the central portion 22c of the fusion cage 22. However, it should be understood that the inner chamber 40 may include any number of compartments, including a single compartment, two compartments, or four or more compartments. In the illustrated embodiment of the invention, each of the chamber compartments 90a, 90b, 90c extends laterally through the fusion cage 22, thereby providing increased flexibility for expansion of the fusion cage 22 and also providing the fusion cage 22 with open sides to permit bone growth into the inner chamber 40 from lateral directions.

In the illustrated embodiment of the fusion cage 22, the end compartments 90a, 90b each have a generally oblong shape or an oval/elliptical configuration, with the inner surfaces of the upper and lower walls 30, 32 adjacent the intermediate compartment 90c tapering inwardly toward one another to define a pair of opposing ramped surfaces 92a, 92b. The center compartments 90c has an arcuate configuration, with the inner surfaces of the upper and lower walls 30, 32 defining a pair of opposing concave surfaces 94a, 94b having substantially the same curvature as the outer surface 100 of the expansion pin 24 (FIG. 5). The point of intersection between the ramped surfaces 92a, 92b of the end compartments 90a, 90b and the concave surfaces 94a, 94b of the center compartment 90c defines opposing apices or vertices 96a, 96b and 98a, 98b positioned on either side of the center compartment 90c. Although the illustrated embodiment of the fusion cage 22 depicts the inner chamber 40 and the compartments 90a, 90b and 90c as having a particular shape and configuration, it should be understood that other suitable shapes and configurations are also contemplate as falling within the scope of the present invention.

Referring to FIG. 5, shown therein is the expansion member 24 according to one embodiment of the present invention. In the illustrated embodiment, the expansion member 24 is configured as an elongate pin having a curved outer surface 100 and defining a generally circular outer cross section having an outer diameter $d_1$. However, it should be understood that other shapes and configurations of the expansion pin 24 are also contemplated for use in association with the present invention such as, for example, elliptical, rectangular or hexagonal-shaped pins. As will be discussed in greater detail below, the curved outer surface 100 of the expansion pin 24 slides along the ramped surfaces 92a, 92b of the upper and lower walls 30, 32 during axial displacement of the expansion pin 24 along the inner chamber 40 to transition the fusion cage 22 to an expanded configuration. Additionally, an aperture 102 extends at least partially through the expansion pin 24 and is sized to receive a distal end portion of a surgical instrument therein to displace and guide the expansion pin 24 along the inner chamber 40 of the fusion cage 22. In one embodiment, the aperture 102 has a generally circular cross section and is threaded to provide for threading engagement with the distal portion of the surgical instrument. However, it should be understood that other shapes and configurations of the aperture 102 are also contemplated for use in association with the present invention.

Referring now to FIG. 6, shown therein is the intervertebral implant 20 positioned within the disc space between the upper and lower vertebral bodies $V_U$, $V_L$ in an initial, non-expanded configuration. A surgical instrument 200 according to one embodiment of the invention is engaged to the intervertebral implant 20 to aid in insertion of the implant 20 into the disc space and transitioning of the fusion cage 22 to the expanded configuration illustrated in FIG. 7. In the illustrated embodiment, the surgical instrument 200 generally includes an outer sleeve 202 and an inner drive shaft 204. The surgical instrument 200 may also include a handle (not shown) to aid in the manipulation and handling of the intervertebral implant 20. However, it should be understood that other suitable types and configurations of surgical instruments are also contemplated for use in association with the present invention, and that the elements and operation thereof may differ from the embodiment of the surgical instrument 200 illustrated and described herein. For example, another type of instrument suitable for use in association with the present invention is illustrated and described in U.S. Pat. No. 6,436,140 to Liu et al., the entire contents of which are hereby incorporated herein by reference.

The outer sleeve 202 of the surgical instrument 200 has a distal end portion 202a adapted for secure engagement to the fusion cage 22. In one embodiment of the invention, the instrument 200 may include a pair of prongs (not shown) extending axially from the distal end portion of the sleeve 202 and including transverse flanges (not shown) extending inwardly toward one another in an opposing manner. As should be appreciated, positioning of the transverse flanges into either of the end compartment 90a, 90c of the fusion cage 22 would function to secure the outer sleeve 202 to the fusion cage 22. However, it should be understood that other types of engagement between the sleeve 202 and the fusion cage 22 are also contemplated such as, for example, threaded engagement, abutting engagement, clamping engagement, keyed engagement, tongue-and-groove engagement, frictional engagement, or any other suitable means for engagement.

The inner drive shaft 204 is disposed within the outer sleeve 202 and includes a distal end portion 204a that extends through the axial opening 82 in the end wall 34 of the fusion cage 22 and into engagement with the expansion pin 24. As indicated above, in one embodiment, the distal end portion 204a of the drive shaft 204 is threadedly engaged within a threaded aperture 102 formed in the expansion pin 24 to securely engage the drive shaft 204 to the expansion pin 24. However, it should be understood that in another embodiment, the distal end portion 204a of the drive shaft 204 and the aperture 102 in the expansion pin 24 need not necessarily be threaded, but may instead define substantially smooth outer and inner surfaces, respectively. It should also be understood that other types of engagement between the drive shaft 204 and the fusion cage 22 are also contemplated, such as, for example, abutting engagement, clamping engagement, keyed engagement, tongue-and-groove engagement, frictional engagement, or any other suitable means for engagement.

As should be appreciated, axial displacement of the drive shaft 204 in the direction of arrow A will correspondingly displace the expansion pin 24 through the inner chamber 40 to transition the fusion cage 22 toward the fully expanded configuration illustrated in FIG. 7. In one embodiment, the drive shaft 204 may be axially displaced via threading engagement between the drive shaft 204 and the outer sleeve 202 as illustrated, for example, in U.S. Pat. No. 6,436,140 to Liu et al. In this manner, rotation of the drive shaft 204 results in axial displacement of the expansion pin 24. In another embodiment, the drive shaft 204 may be generally configured as a screw or bolt threadingly engaged within the axial opening 82 in the end wall 34 of the fusion cage 22 such that rotation of the drive shaft 204 results in axial displacement of the expansion pin 24. It should be understood, however, that other suitable devices and techniques for axially displacing the expansion pin 24 through the inner chamber 40 of the fusion cage 22 are also contemplated as falling within the scope of the present invention.

As should be appreciated, axial displacement of the expansion pin 24 from the end compartment 90a toward the center compartment 90c of the inner chamber 40 slidably engages the outer surface 100 of the expansion pin 24 against the ramped surfaces 92a, 92b. As a result, the upper and lower walls 30, 32 of the fusion cage 22 are driven away from one another and are outwardly deformed along the transverse axis T to transition the fusion cage 22 from the initial, non-expanded configuration illustrated in FIG. 6 toward the expanded configuration illustrated in FIG. 7. The expansion pin 24 is further displaced in an axial direction until positioned within the center compartment 90c of the inner chamber 40, with the expansion pin 24 positioned within the recessed areas formed by the opposing concave surfaces 94a, 94b and captured between the opposing apices/vertices 96a, 96b and 98a, 98b.

It should be appreciated that positioning of the expansion pin 24 within the opposing concave surfaces 94a, 94b and between the opposing apices/vertices 96a, 96b and 98a, 98b retains the expansion pin 24 within the center compartment 90c and inhibits further axial displacement of the expansion pin 24 to thereby maintain the fusion cage 22 in the expanded configuration illustrated in FIG. 7, even after the drive shaft 204 is detached from the expansion pin 24. It should also be appreciated that during expansion of the fusion cage 22, once the expansion pin 24 is positioned beyond the pair of opposing apices/vertices 96a, 96b and enters the center compartment 90c, the amount of linear driving force or rotational torque exerted onto the drive shaft 204 of the instrument 200 will abruptly decrease. This abrupt drop-off in driving force or torque provides the surgeon with a perceptible indication that the expansion pin 24 is properly positioned within the central compartment 90c and that the desired amount of expansion has been attained.

As illustrated in FIG. 6, the fusion cage 22 has an initial, non-expanded height $h_1$ that is somewhat less than the distance separating the upper and lower vertebral bodies $V_U$, $V_L$ (i.e., the disc space height). However, as illustrated in FIG. 7, expansion of the fusion cage 22 increases the overall height of the fusion cage 22 to an expanded height $h_2$ that is substantial equal to the height of the disc space. As should be appreciated, the difference between the initial height $h_1$ and the expanded height $h_2$ of the fusion cage 22 corresponds to the difference between the diameter $d_1$ (or height) of the expansion pin 24 (FIG. 5) and the non-expanded distance $d_2$ between the concave surfaces 94a, 94b of the center compartment 90c of the fusion cage 22 (FIG. 6). Accordingly, expansion of the fusion cage 22 can be easily and accurately controlled by providing an expansion pin 24 having a select diameter $d_1$ (or height) and/or by providing the center compartment 90c with a configuration having a select non-expanded distance $d_2$ between the concave surfaces 94a, 94b.

In the illustrated embodiment of the invention, axial displacement of the expansion pin 24 through the inner chamber 40 results in expansion of the fusion cage 22 along the transverse axis T. However, it should be understood that in other embodiments of the invention, the fusion cage 22 and the expansion pin 24 may be configured such that transverse, rotational and/or pivotal displacement of the expansion pin 24 relative to fusion cage 22 serves to expand the fusion cage 22 along the transverse axis T. For example, in an alternative embodiment of the invention, the expansion pin 24 may be configured to have an oblong or cam-like configuration such that rotation of the expansion pin 24 within the center compartment 90c results in expansion of the fusion cage 22. Additionally, although the illustrated embodiment of the invention depicts expansion of the fusion cage 22 in response to pushing or driving the expansion pin 24 axially through the inner chamber 40 from the end compartment 90a toward the center compartment 90c, it should be understood that the fusion cage 22 may be expanded in response to pulling or drawing the expansion pin 24 axially through the inner chamber 40 from the end compartment 90b toward the center compartment 90c.

As illustrated in FIG. 7, when the fusion cage 22 is transitioned to the expanded configuration, the upper and lower walls 30, 32 are outwardly deformed away from one another along the transverse axis T to increase the overall height $h_2$ of the fusion cage 22. Since the end portions of the upper and lower walls 30, 32 are integrally connected to the end walls 34, 36, the end portions of the upper and lower walls 30, 32 remain relatively stationary and expansion of the fusion cage 22 adjacent the end portions 22a, 22b is limited. However, since the central portions of the upper and lower walls 30, 32 are not interconnected, expansion of the fusion cage 22 occurs primarily along the central portion of the fusion cage 22. As a result, upon expansion of the fusion cage 22, the upper and lower walls 30, 32 each form a convex curvature extending along the longitudinal axis L. The convex curvature of the outwardly deformed upper and lower walls 30, 32 substantially corresponds to the anterior-to-posterior surface curvature C defined by the vertebral endplates of the adjacent vertebral bodies $V_U$, $V_L$. Following expansion of the fusion cage 22, the surgical instrument 200 is disengaged from the intervertebral implant 20 and removed from the patient.

In a further aspect of the invention, a bone growth promoting material 300 (FIGS. 7 and 8) is loaded into the inner chamber 40 of the fusion cage 22 to facilitate or promote bone growth from the upper and lower vertebral bodies $V_U$, $V_L$, through the upper and lower bone growth openings 80a, 80b, and into and possibly through the fusion cage 22. In one embodiment, the bone growth promoting material 300 comprises of a bone graft material, a bone morphogenic protein (BMP), or any other suitable bone growth promoting material or substance, including but not limited to bone chips or bone marrow, a demineralized bone matrix (DBM), mesenchymal stem cells, and/or a LIM mineralization protein (LMP). It should be understood that the bone growth promoting material 300 can be used with or without a suitable carrier.

In one embodiment of the invention, the bone growth promoting material 300 is injected into the inner chamber 40 via the axial openings 82 in the end wall 34 subsequent to expansion of the fusion cage 22. In another embodiment, the bone growth promoting material 300 may be pre-loaded into the end compartment 90b of the inner chamber 40 prior to insertion and expansion of the fusion cage 22 (when the expansion pin 24 is initially positioned within the end compartment 90a). In a further embodiment, the fusion cage 22 and the expansion pin 24 may be configured to allow pre-loading of the bone growth promoting material 300 into each of the end compartments 90a, 90b prior to insertion and expansion of the fusion cage 22.

Having illustrated and described the elements and operation of the intervertebral implant 20, reference will now be made to a technique for implanting the intervertebral implant 20 within a disc space according to one embodiment of the invention. However, it should be understood that other implantation techniques and procedures are also contemplated, and that the following technique in no way limits the scope of the present invention.

In one embodiment of the invention, access to the spinal column and insertion of the intervertebral implant 20 into the disc space is accomplished via a posterior surgical approach. However, it should be understood that access and insertion of the intervertebral implant 20 into the disc space may be accomplished via other surgical approaches such as, for example, an anterior approach or a lateral approach. In another embodiment of the invention, the intervertebral implant 20 is used to treat the lumbar region of the spine, with the upper and lower vertebral bodies $V_U, V_L$ comprising lumbar vertebral bodies. However, it should be understood that the present invention is also applicable to other portions of the spine such as, for example, the cervical, thoracic or sacral regions of the spinal column.

Initially, the portion of the spinal column to be treated is identified and accessed from a posterior approach using known surgical techniques. At least a portion of the natural intervertebral disc is removed via a total or partial discectomy to provide an opening for receiving the intervertebral implant 20 between the upper and lower vertebral bodies $V_U, V_L$. The disc space is then distracted to a height substantially equal to the natural disc space height. Prior to insertion of the intervertebral implant 20, the disc space and the endplates of the upper and lower vertebral bodies $V_U$ and $V_L$ are prepared using various cutting tools and/or other types of surgical instruments (e.g., curettes, chisels, etc.). One example of a cutting instrument suitable for preparing the vertebral bodies $V_U, V_L$ is illustrated and described in U.S. Pat. No. 6,610,089 to Liu et al., the contents of which have bee incorporated herein by reference. However, it should be understood that other types and configurations of cutting instruments are also contemplated for use in association with the present invention.

In one embodiment of the present invention, the cutting instrument used to prepare the vertebral bodies $V_U, V_L$ is adapted to cut and remove bone tissue from the vertebral endplates while substantially retaining the natural concave curvature of the endplates and avoiding cutting into the cortical rim/apophyseal ring region adjacent the anterior/posterior portions of the vertebral endplates. The cutting instrument may also be configured to collect bony debris or chips generated during the cutting operation for subsequent insertion into the inner chamber 40 of the fusion cage 22 to promote arthrodesis. As illustrated in FIGS. 6 and 7, each of the prepared vertebral endplates defines a recessed area or surface curvature C that is generally concave in an anterior-to-posterior direction. As should be appreciated, the recessed area or surface curvature C defined by the vertebral bodies $V_U, V_L$ receives the outwardly deformed upper and lower walls 30, 32 of the expanded fusion cage 22 so as to position the upper and lower surfaces 50, 52 of the fusion cage and the bone growth material 300 positioned within the fusion cage 22 in close proximity to the spongy cancellous bone tissue of the vertebral bodies $V_U, V_L$ to promote fusion.

Following preparation of the vertebral endplates, the intervertebral implant 20 is inserted into the disc space using a suitable insertion technique such as, for example, impaction or push-in type insertion. Notably, since the intervertebral implant 20 is inserted into the disc space while in a non-expanded configuration having an initial height $h_1$ that is somewhat less than the disc space height, over distraction of the disc space is avoided and neural distraction is minimized. In a further embodiment of the invention, the intervertebral implant 20 may be inserted into the disc space in a minimally invasive manner (i.e., through a small access portal) via the use of endoscopic equipment, a small diameter tube or cannula, or by other minimally invasive surgical techniques. However, it should be understood that the implant 20 may be inserted into the disc space using conventional surgical methods and techniques. Following insertion of the intervertebral implant 20 into the disc space, the fusion cage 22 is expanded to the configuration illustrated in FIG. 7 (having an expanded height $h_2$) to restore and/or maintain a desired disc space height. As discussed above, transitioning of the fusion cage 22 to the expanded configuration results in outward deformation of the upper and lower walls 30, 32 from the substantially planar configuration illustrated in FIG. 6 to the arcuate or curved configuration illustrated in FIG. 7.

Figure 8:
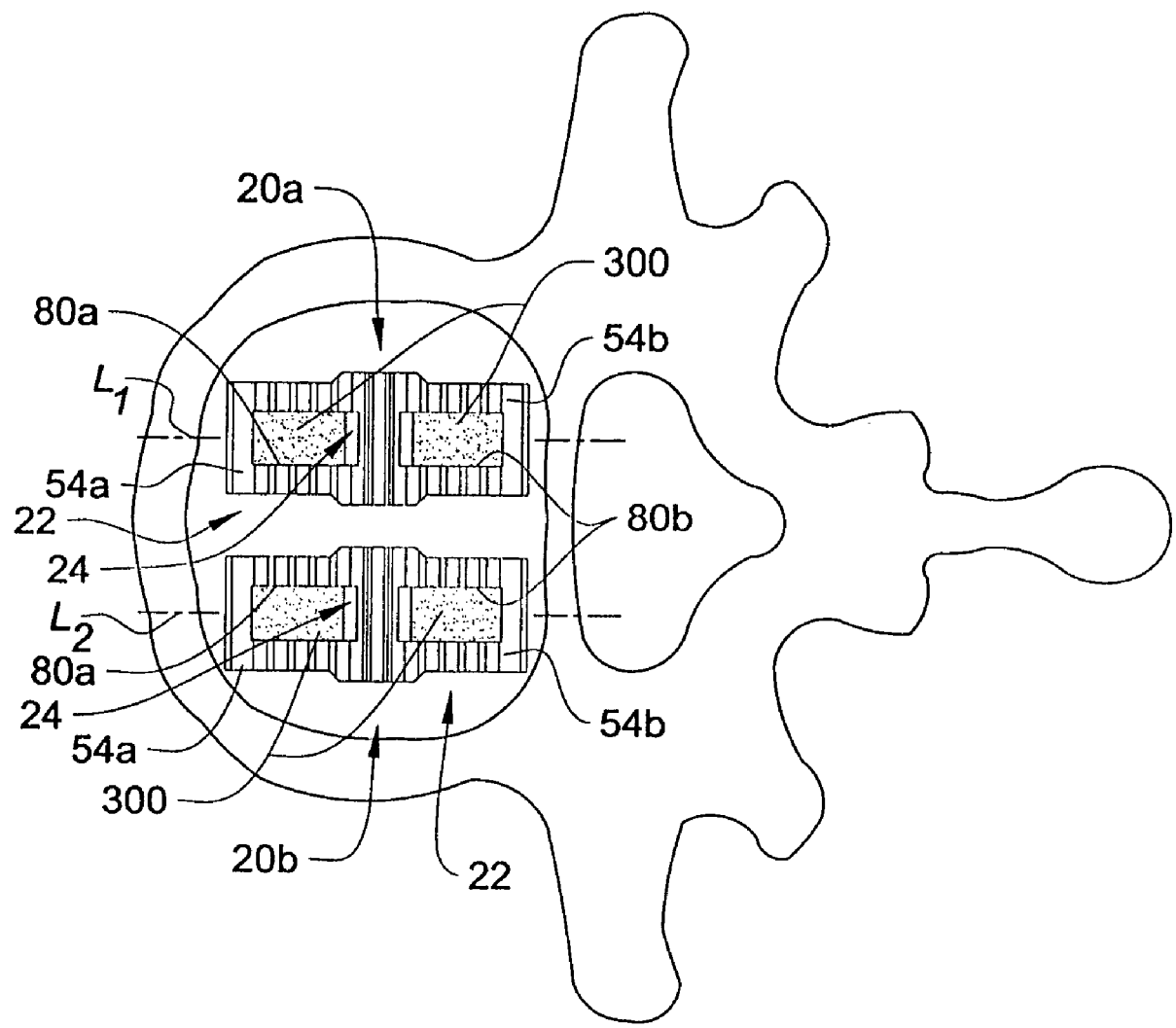
FIG. 8 is a top plan view of a pair of the intervertebral implants illustrated in FIG. 1, as positioned side-by-side in a bilateral arrangement within a disc space.

As should be appreciated, a vertebra is comprised of a hard cortical bone material extending about the outer region of the vertebral body, and a softer cancellous or spongiose bone material within of the cortical bone material. As illustrated in FIGS. 7 and 8, the upper and lower anterior/posterior bearing surfaces 54a, 54b and 56a, 56b of the fusion cage 22 are positioned to bear against the cortical rim/apophyseal ring region of the respective upper and lower vertebral bodies $V_U$, $V_L$ to resist the compressive forces exerted onto the fusion cage 22 and to reduce the likelihood of subsidence into the relatively softer cancellous or spongiseum bone tissue. Additionally, transitioning of the fusion cage to the expanded configuration illustrated in FIG. 7 imbeds or impacts the teeth 60 extending form the upper and lower surfaces 50, 52 into the vertebral endplates to resist migration and possible expulsion of the fusion cage 22 from the disc space. Moreover, positioning of the outwardly deformed upper and lower walls 30, 32 within the concave surface curvature C defined by the upper and lower vertebral bodies $V_U$, $V_L$ tends to increase stability of the fusion cage 22 and also reduces the likelihood of migration and possible expulsion of the fusion cage 22 from the disc space. Furthermore, positioning of the outwardly deformed upper and lower walls 30, 32 in close proximity to or in direct contact with the cancellous or spongiseum bone tissue of the upper and lower vertebral bodies $V_U$, $V_L$ facilitates bone growth into the grooves 62 and/or through the openings 80a, 80b and into the inner chamber 40.

In a further aspect of the invention, positioning of the expansion pin 24 within the center compartment 90c of the inner chamber 40 provides additional support and rigidity to the upper and lower walls 30, 32 of the fusion cage 22 to resist compression loads from the vertebral bodies $V_U$, $V_L$, particularly near the central portion 22c of the fusion cage 22 which is otherwise devoid of internal support members. Although the intervertebral implant 20 is maintained in the expanded configuration solely via engagement between the expansion pin 24 and the upper and lower walls 30, 32 of the fusion cage 22, it should be understood that one or more supplemental internal fixation elements may also be used to provide further support to the fusion cage 22, particularly in instances involving excessive vertebral loading and/or instability. It should also be understood that supplemental external intravertebral fixation elements and/or stabilization techniques may also be used if excessive residual instability is encountered following insertion and expansion of one or more of the intervertebral implants 20 within the disc space.

Once the fusion cage 22 is fully expanded, the bone growth promoting material 300 is loaded into the inner chamber 40 of the fusion cage 22 to facilitate or promote bone growth from the upper and lower vertebral bodies $V_U$, $V_L$, through the bone growth openings 80a, 80b, and into and possibly through the fusion cage 22. Additionally, bone graft, morselized autograft bone or a similar type of material may be positioned laterally adjacent the expanded fusion cage 22 to further promote fusion. As discussed above, in one embodiment of the invention, bone growth promoting material 300 is preloaded into the end compartment 90b of the inner chamber 40 prior to insertion and expansion of the fusion cage, followed by loading of bone growth promoting material 300 into the end compartment 90a of the inner chamber 40 subsequent to insertion and expansion of the fusion cage 22. As a result, bone growth promoting material 300 may be positioned on either side of the expansion pin 24 adjacent the bone ingrowth openings 80a, 80b to facilitate fusion.

Referring to FIG. 8, in a further embodiment of the invention, a pair of intervertebral implants 20a, 20b may be positioned side-by-side in a bilateral arrangement within the disc space. However, it should be understood that unilateral placement or central placement of a single intervertebral implant 20 within the disc space is also contemplated as falling within the scope of the present invention. Bone graft, morselized autograft bone, or a bone growth promoting substance may be positioned within the area between the implants 20a, 20b to further facilitate fusion between the upper and lower vertebral bodies $V_U$, $V_L$.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An expandable intervertebral implant, comprising:
    a body having a longitudinal axis and including first and second axial walls spaced apart along a transverse axis to define an inner chamber, said first axial wall including a first pair of opposite end portions, said second axial wall including a second pair of opposite end portions, said first pair of end portions interconnected with said second pair of end portions; and
    an expansion member engaged with said first and second axial walls at a location intermediate said first and second pairs of opposite end portions and extending transversely between and slidably engaging central portions of said first and second axial walls to expand said body along said transverse axis, said expansion member comprising an internal support member positioned within a central region of said inner chamber and having a height extending transversely between and engaging opposing inner surfaces of said central portions of said first and second axial walls; and
    wherein said expansion member is slidably engaged with said first and second axial walls to uniaxially expand said body along said transverse axis.

2. The implant of claim 1, wherein said body includes first and second transverse end walls extending between and interconnecting said first pair of end portions with said second pair of end portions.

3. The implant of claim 2, wherein said first and second axial walls are formed integral with said first and second transverse end walls to define a unitary body.

4. The implant of claim 1, wherein said body has a generally rectangular axial cross-section.

5. The implant of claim 1, wherein expansion of said body comprises outward deformation of said first and second axial walls along said transverse axis.

6. The implant of claim 5, wherein said outward deformation of said first and second axial walls defines a convex outer curvature extending along said longitudinal axis.

7. The implant of claim 1, wherein movement of said expansion member within said inner chamber engages said expansion member with said first and second axial walls to expand said body along said transverse axis.

8. The implant of claim 1, wherein an outer surface of each of said first and second axial walls includes a number of anchor elements adapted to engage adjacent vertebral bodies.

9. The implant of claim 8, wherein said anchor elements comprise at least one row of teeth extending from said outer surface of each of said first and second axial walls.

10. The implant of claim 9, wherein positioning of said at least one row of teeth is confined to a central portion of said outer surface.

11. The implant of claim 10, wherein said anchor elements comprise at least one groove formed in said outer surface of each of said first and second axial walls.

12. The implant of claim 11, wherein said anchor elements comprise a plurality of grooves formed in said outer surface of each of said first and second axial walls.

13. The implant of claim 11, wherein said at least one groove has an arcuate configuration.

14. The implant of claim 1, wherein said body comprises a pair of opposite end portions having a first width and a central portion having a second width greater than said first width.

15. The implant of claim 1, wherein axial displacement of said expansion member within said inner chamber engages said expansion member with said first and second axial walls to expand said body along said transverse axis, said expansion member slidably engaged along opposing inner surfaces of said first and second axial walls during said axial displacement; and
    wherein said expansion member comprises an elongate pin having a length extending substantially entirely across a width of said inner chamber.

16. An expandable intervertebral implant, comprising:
    a body having a longitudinal axis and including first and second axial walls spaced apart along a transverse axis to define an inner chamber, said first axial wall including a first pair of opposite end portions, said second axial wall including a second pair of opposite end portions, said first pair of end portions interconnected with said second pair of end portions; and
    an expansion member engaged with said first and second axial walls at a location intermediate said first and second pairs of opposite end portions and extending transversely between and engaging central portions of said first and second axial walls to expand said body along said transverse axis, said expansion member comprising an internal support member positioned within a central region of said inner chamber and having a height extending transversely between and engaging opposing inner surfaces of said central portions of said first and second axial walls; and
    wherein movement of said expansion member within said inner chamber engages said expansion member with said first and second axial walls to expand said body along said transverse axis, and wherein said movement of said expansion member within said inner chamber comprises axial displacement generally along said longitudinal axis, said expansion member slidably engaged along opposing inner surfaces of said first and second axial walls during said axial displacement.

17. The implant of claim 16, wherein said first and second axial walls have inner surfaces facing said inner chamber, at least one of said inner surfaces defining a recessed area for receiving said expansion member upon expansion of said body along said transverse axis.

18. The implant of claim 17, wherein said inner surfaces of said first and second axial walls define opposing recessed areas for receiving said expansion member upon expansion of said body along said transverse axis.

19. The implant of claim 17, wherein said recessed area retains said expansion member in a select axial position upon expansion of said body along said transverse axis.

20. The implant of claim 19, wherein said select axial position is adjacent said central region of said inner chamber.

21. The implant of claim 16, wherein said first and second axial walls have inner surfaces facing said inner chamber, said inner surfaces defining an inward taper along said longitudinal axis, said expansion member slidably engaged along said inward taper to expand said body along said transverse axis as said expansion member is displaced generally along said longitudinal axis.

22. The implant of claim 21, wherein said inner surfaces of said first and second axial walls include opposing ramp portions defining said inward taper.

23. The implant of claim 16, wherein at least one of said first and second axial walls includes a retention element adapted to engage and retain said expansion member in a select axial position upon expansion of said body along said transverse axis.

24. The implant of claim 16 further comprising a bone growth promoting substance positioned within said inner chamber to facilitate fusion with adjacent vertebral bodies.

25. The implant of claim 24, wherein each of said first and second axial walls defines at least one bone in-growth opening extending therethrough and communicating with said inner fusion chamber.

26. The implant of claim 24, wherein said bone growth promoting substance is positioned within first and second end portions of said inner chamber on opposite sides of said expansion member.

27. The implant of claim 26, wherein each of said first and second axial walls defines a first bone in-growth opening extending therethrough and communicating with said first end portion of said inner chamber, and a second bone in-growth opening extending therethrough and communicating with said second end portion of said inner chamber.

28. The implant of claim 24, wherein said bone growth promoting substance comprises a bone morphogenic protein.

29. An expandable intervertebral implant, comprising:
a body having an implant length extending along a longitudinal axis and an implant width, said body including first and second axial walls extending generally along said longitudinal axis and spaced apart along a transverse axis, said body including first and second transverse end walls extending between and interconnecting opposing end portions of said first and second axial walls, said axial walls and said transverse end walls defining generally flat and planar upper and lower vertebral bearing surfaces extending substantially entirely across said implant width; and
an expansion member slidably engaged with said first and second axial walls to expand said body along said transverse axis such that said first and second axial walls are outwardly deformed to define a convex outer curvature extending along said implant length;
wherein said body defines an inner chamber sized to receive said expansion member therein; and
wherein movement of said expansion member within said inner chamber slidably engages said expansion member with said first and second axial walls at a location intermediate said first and second transverse end walls and extending transversely between and slidably engaging central portions of said first and second axial walls to outwardly deform said first and second axial walls along said transverse axis.

30. The implant of claim 29, wherein said movement of said expansion member within said inner chamber comprises axial displacement generally along said longitudinal axis, said expansion member slidably engaged along opposing inner surfaces of said first and second axial walls during said axial displacement.

31. The implant of claim 30, wherein each of said first and second axial walls defines at least one bone in-growth opening extending therethrough and communicating with said inner chamber; and
further comprising a bone growth promoting substance positioned within said inner chamber to facilitate fusion with adjacent vertebral bodies.

32. The implant of claim 29, wherein said expansion member comprises an internal support member positioned within a central region of said inner chamber and having a height extending transversely between and engaging opposing inner surfaces of said central portions of said first and second axial walls.

33. An expandable intervertebral implant, comprising:
a body having a longitudinal axis and including first and second axial walls spaced apart along a transverse axis to define an inner chamber, said body including first and second transverse end walls extending between and interconnecting opposing end portions of said first and second axial walls; and
an expansion member engaged with said first and second axial walls at a location intermediate said first and second transverse end walls and extending transversely between and engaging central portions of said first and second axial walls to transition said body from an initial configuration to an expanded configuration wherein said first and second axial walls are outwardly deformed away from one another along said transverse axis, said expansion member comprising an internal support member positioned within a central region of said inner chamber and having a height extending transversely between and engaging opposing inner surfaces of said central portions of said first and second axial walls; and
wherein said first and second axial walls define a convex outer curvature along said longitudinal axis when transitioned to said expanded configuration; and
wherein movement of said expansion member within said inner chamber engages said expansion member with said first and second axial walls to transition said body to said expanded configuration, and wherein said movement of said expansion member within said inner chamber comprises axial displacement generally along said longitudinal axis, said expansion member slidably engaged along opposing inner surfaces of said first and second axial walls during said axial displacement.

34. An expandable intervertebral implant, comprising:
a body having a longitudinal axis and including first and second axial walls spaced apart along a transverse axis to define an inner chamber, said body including first and second transverse end walls extending between and interconnecting opposing end portions of said first and second axial walls; and an expansion member engaged with said first and second axial walls at a location intermediate said first and second transverse end walls and extending transversely between and slidably engaging central portions of said first and second axial walls to transition said body from an initial configuration to an expanded configuration wherein said first and second axial walls are outwardly deformed away from one another along said transverse axis, said expansion member comprising an internal support member positioned within a central region of said inner chamber and having a height extending transversely between and engaging opposing inner surfaces of said central portions of said first and second axial walls; and wherein said expansion member is slidably engaged with said first and second axial walls to outwardly deform and uni-axially expand said first and second axial walls along said transverse axis.

35. The implant of claim 34, wherein said first and second axial walls define a convex outer curvature along said longitudinal axis when transitioned to said expanded configuration.

36. The implant of claim 35, wherein movement of said expansion member within said inner chamber engages said expansion member with said first and second axial walls to transition said body to said expanded configuration.

37. The implant of claim 36, wherein at least one of said transverse end walls defines a tool receiving opening in communication with said inner chamber and sized to receive portion of a surgical instrument therethrough for engagement with said expansion member.

38. The implant of claim 34 wherein each of said first and second axial walls defines at least one bone in-growth opening extending therethrough and communicating with said inner chamber; and further comprising a bone growth promoting substance positioned within said inner chamber to facilitate fusion with adjacent vertebral bodies.

39. The implant of claim 38, wherein said bone growth promoting substance comprises a bone morphogenic protein.

40. An expandable intervertebral implant, comprising:
a fusion cage having a longitudinal axis and including first and second axial walls extending generally along said longitudinal axis and spaced apart along a transverse axis, said fusion cage defining an inner chamber having a central portion and opposite first and second end portions;

an expansion member positioned within said central portion of said inner chamber and engaged with said first and second axial walls at a location intermediate said first and second end portions of said inner chamber and extending transversely between and slidably engaging central portions of said first and second axial walls to expand said fusion cage along said transverse axis, said expansion member comprising an internal support member positioned within a central region of said inner chamber and having a height extending transversely between and slidably engaging opposing inner surfaces of said central portions of said first and second axial walls; and a bone growth promoting material positioned within said first and second end portions of said inner chamber on opposite sides of said expansion member; and wherein expansion of said body comprises outward deformation and uni-axial expansion of said first and second axial walls along said transverse axis.

41. The implant of claim 40, wherein each of said first and second axial walls defines a first bone in-growth opening extending therethrough and communicating with said first end portion of said inner chamber, and a second bone in-growth opening extending therethrough and communicating with said second end portion of said inner chamber.

42. The implant of claim 40, wherein said bone growth promoting substance comprises a bone morphogenic protein.

43. The implant of claim 40, wherein said outward deformation of said first and second axial walls defines a convex outer curvature extending along said longitudinal axis.

44. A surgical method, comprising:
providing an expandable intervertebral implant having a longitudinal axis and including first and second axial walls spaced apart along a transverse axis, the body including first and second transverse end walls extending between and interconnecting opposing end portions of the first and second axial walls;

inserting the intervertebral implant within an intervertebral space with the first and second axial walls positioned adjacent respective first and second vertebral bodies;

positioning an expansion member between the first and second axial walls; and expanding the intervertebral implant along the transverse axis by slidably engaging the expansion member along opposing inner surfaces of the first and second axial walls in a direction along the longitudinal axis to a location intermediate the first and second transverse end walls with the expansion member extending transversely between and engaging mid-portions of the first and second axial walls to engage the first and second axial walls against the respective first and second vertebral bodies.

45. The method of claim 44, wherein the intervertebral implant defines an inner chamber extending along the longitudinal axis; and further comprising positioning a bone growth promoting material within the inner chamber.

46. The method of claim 44, wherein the intervertebral implant defines an inner chamber extending along the longitudinal axis; and wherein the expansion member comprises an internal support member positioned within a central region of the inner chamber and having a height extending transversely between and engaging the opposing inner surfaces of the mid-portions of the first and second axial walls.

47. The method of claim 46, wherein the inner chamber has opposite first and second end portions; and wherein moving the expansion member within the central portion of the inner chamber results in uni-axial expansion of the first and second axial walls along the transverse axis.

48. The method of claim 47, further comprising positioning a bone growth promoting material within the first and second end portions of the inner chamber on opposite sides of the expansion member.

49. The method of claim 48, wherein each of the first and second axial walls defines a first bone in-growth opening extending therethrough and communicating with the first end portion of the inner chamber, and a second bone in-growth opening extending therethrough and communicating with the second end portion of the inner chamber.

50. The method of claim 44, wherein the expanding comprises outwardly deforming the first and second axial walls to define a convex outer curvature extending along the longitudinal axis.

51. The method of claim 44, wherein each of the first and second axial walls includes first and second end portions disposed adjacent the first and second transverse end walls; and wherein the expanding comprises outwardly deforming the first and second axial walls away from one other such that expansion of the mid-portions of the first and second axial walls is greater than expansion of the end portions of the first and second axial walls.

52. The method of claim 44, further comprising preparing a disc space between the first and second vertebral bodies prior to the insertion including removing a portion of the cortical bone from each of the first and second vertebral bodies to expose cancellous bone tissue while substantially maintaining the cortical rim region intact; and wherein the expanding engages the first and second axial walls against the exposed cancellous bone tissue of the first and second vertebral bodies.

53. The method of claim 52, wherein the inserting includes positioning upper and lower bearing surfaces of the first and second transverse end walls adjacent the cortical rim region of the first and second vertebral bodies.

54. The method of claim 52, wherein the removing of cortical bone comprises forming a concave recess in each of the adjacent vertebral bodies; and wherein the expanding comprises outwardly deforming each of the first and second axial walls to define a convex outer curvature received within the concave recess of a respective one of the first and second vertebral bodies.

* * * * *